United States Patent [19]

Johnson et al.

[11] 4,191,822

[45] * Mar. 4, 1980

[54] 5-HYDROXY-PGI$_1$ COMPOUNDS

[75] Inventors: Roy A. Johnson; John C. Sih, both of Kalamazoo, Mich.

[73] Assignee: The Upjohn Company, Kalamazoo, Mich.

[*] Notice: The portion of the term of this patent subsequent to Aug. 29, 1995, has been disclaimed.

[21] Appl. No.: 919,894

[22] Filed: Jun. 28, 1978

Related U.S. Application Data

[63] Continuation-in-part of Ser. No. 815,648, Jul. 14, 1977, Pat. No. 4,110,532.

[51] Int. Cl.$^2$ ............................................ C07D 307/93
[52] U.S. Cl. ..................................... 542/416; 542/421; 542/426; 542/429; 260/343.21; 260/343.5; 260/346.22; 260/346.73
[58] Field of Search ........... 260/343.21, 343.5, 346.22, 260/346.73; 542/416, 421, 422, 426, 429, 430, 431

[56] References Cited

PUBLICATIONS

Johnson et al., Prostaglandins 12, 915 (1976).

*Primary Examiner*—Alan L. Rotman
*Assistant Examiner*—Bernard Dentz
*Attorney, Agent, or Firm*—Robert A. Armitage

[57] ABSTRACT

This invention relates to certain structural analogs of 5,6-dihydroprostacyclin (PGI$_1$) wherein the C-5 carbon atom is substituted by hydroxy. These novel 5-hydroxy-prostacyclin-type compounds are smooth muscle stimulators.

1 Claim, No Drawings

5-HYDROXY-PGI₁ COMPOUNDS

The present application is a continuation-in-part of Ser. No. 815,648, filed July 14, 1977, issued as U.S. Pat. No. 4,110,532 on Aug. 29, 1978.

The essential material constituting a disclosure for the preparation and use of the present invention is incorporated here by reference from U.S. Pat. No. 4,110,532.

BACKGROUND OF THE INVENTION

This invention relates to novel structural analogs of 5,6-dihydroprostacyclin ($PGI_1$). In particular, the present invention relates to prostacyclin-type compounds wherein the C-5 carbon atom of 5,6-dihydroprostacyclin is substituted by a hydroxy.

SUMMARY OF THE INVENTION

The present invention particularly comprises:
A prostacyclin analog of the formula

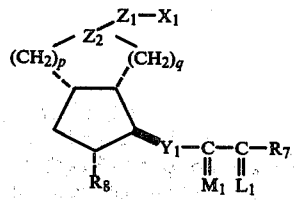

IV wherein $R_7$ is
(1) —$(CH_2)_m$—$CH_3$,

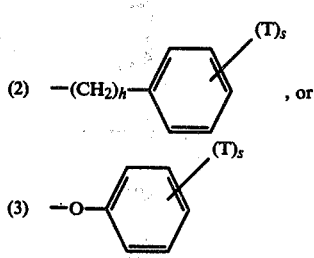

(2) —$(CH_2)_h$—[phenyl]—$(T)_s$, or (3) —O—[phenyl]—$(T)_s$ wherein m is the integer one to 5, inclusive, h is the integer zero to 3, inclusive; s is the integer zero, one, 2 or 3, and T is chloro, fluoro, trifluoromethyl, alkyl of one to 3 carbon atoms, inclusive, or with the proviso that not more than two T's are other than alkyl;
wherein $Z_2$ is

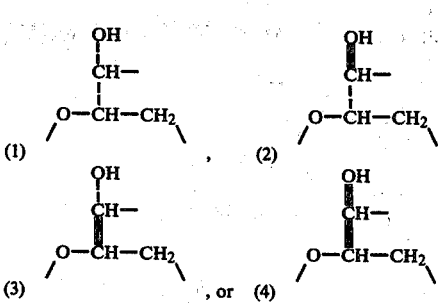

wherein one of p or q is the integer zero or one and the other is the integer zero;
wherein $Z_1$ is
(1) —$(CH_2)_g$—$CH_2$—$CH_2$—,
(2) —$(CH_2)_g$—$CH_2$—$CF_2$—, or
(3) trans—$(CH_2)_g$—CH=CH—,
wherein g is the integer one, 2, or 3 when q is zero and zero, one, or 2 when q is one;
wherein $R_8$ is hydrogen, hydroxy, or hydroxymethyl;
wherein $Y_1$ is
(1) trans—CH=CH—,
(2) cis—CH=CH—,
(3) —$CH_2CH_2$—,
(4) trans—CH=C(Hal)—, or
(5) —C≡C—
wherein Hal is chloro or bromo;
wherein $M_1$ is

wherein $R_5$ is hydrogen or alkyl with one to 4 carbon atoms, inclusive;
wherein $L_1$ is

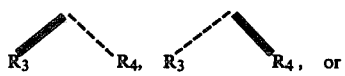

a mixture of

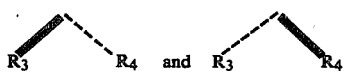

wherein $R_3$ and $R_4$ are hydrogen, methyl, or fluoro, being the same or different, with the proviso that one of $R_3$ and $R_4$ is fluoro only when the other is hydrogen or fluoro;
wherein $X_1$ is
(1) —$COOR_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
(2) —$CH_2OH$,
(3) —$CH_2NL_2L_3$, wherein $L_2$ and $L_3$ are hydrogen, alkyl of one to 4 carbon atoms, inclusive, or —$COOR_1$, wherein $R_1$ is as defined above;
(4) —$COL_4$, wherein $L_4$ is
(a) amino of the formula —$NR_{21}R_{22}$, wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;
(b) cycloamino selected from the group consisting of

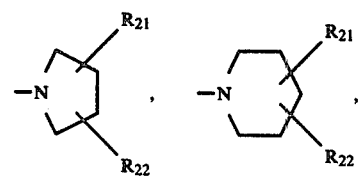

-continued wherein R₂₁ and R₂₂ are as defined above;

(c) carbonylamino of the formula —NR₂₃COR₂₁, wherein R₂₃ is hydrogen or alkyl of one to 4 carbon atoms and R₂₁ is as defined above;

(d) sulphonylamino of the formula —NR₂₃SO₂R₂₁, wherein R₂₁ and R₂₃ are as defined above; or (5) —COOL₅, wherein L₅ is p-substituted phenyl selected from the group consisting of wherein R₂₄ is methyl, phenyl, acetamidophenyl, benzamidophenyl, or —NH₂; R₂₅ is methyl, phenyl, —NH₂, or methoxy; and R₂₆ is hydrogen or acetamido; and the 1,5- and 1,15-lactones thereof.

We claim:

1. A prostacyclin analog of the formula wherein R₇ is (1) —(CH₂)ₘ—CH₃, (2) —(CH₂)ₕ—⌬(T)ₛ , (3) —O—⌬(T)ₛ wherein m is the integer one, 2, 4, or 5; h is the integer 2 or 3; s is the integer zero, one, 2, or 3, and T is chloro, fluoro, trifluoromethyl, alkyl of one to 3 carbon atoms, inclusive, or with the proviso that not more than two T's are other than alkyl;

wherein Z₂ is wherein Z₁ is (1) —(CH₂)_g—CH₂—CH₂—,
(2) —(CH₂)_g—CH₂—CF₂—, or
(3) trans—(CH₂)_q—CH=CH—, wherein R₈ is hydrogen, hydroxy, or hydroxymethyl;

wherein Y₁ is (1) trans—CH=CH—,
(2) cis—CH=CH—,
(3) —CH₂CH₂—,
(4) trans—CH=C(Hal)—, or
(5) —C≡C— wherein Hal is chloro or bromo;

wherein M₁ is wherein R₅ is hydrogen or alkyl with one to 4 carbon atoms, inclusive;

wherein $L_1$ is

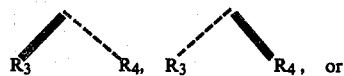

a mixture of

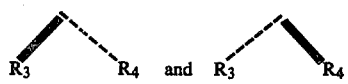

wherein $R_3$ and $R_4$ are hydrogen, methyl, or fluoro, being the same or different, with the proviso that one of $R_3$ and $R_4$ is fluoro only when the other is hydrogen or fluoro;

wherein $X_6$ is
  (1) $-COOR_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation,
  (2) $-CH_2OH$,
  (3) $-CH_2NL_2L_3$, wherein $L_2$ and $L_3$ are hydrogen, alkyl of one to 4 carbon atoms, inclusive, or $-COOR_1$, wherein $R_1$ is as defined above;
  (4) $-COL_4$, wherein $L_4$ is
    (a) amino of the formula $-NR_{21}R_{22}$, wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;
    (b) carbonylamino of the formula $-NR_{23}COR_{21}$, wherein $R_{23}$ is hydrogen or alkyl of one to 4 carbon atoms and $R_{21}$ is as defined above; or
    (c) sulphonylamino of the formula $-NR_{23}SO_2R_{21}$, wherein $R_{21}$ and $R_{23}$ are as defined above; or
  (5) $-COOL_5$, wherein $L_5$ is p-substituted phenyl selected from the group consisting of

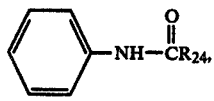

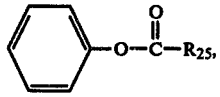

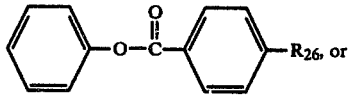

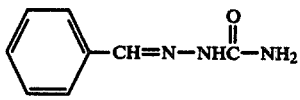

wherein $R_{24}$ is methyl, phenyl, acetamidophenyl, benzamidophenyl, or $-NH_2$; $R_{25}$ is methyl, phenyl, $-NH_2$, or methoxy; and $R_{26}$ is hydrogen or acetamido, and the 1,5- and 1,15-lactones thereof.

* * * * *